(12) United States Patent
Nozaki

(10) Patent No.: US 11,571,699 B2
(45) Date of Patent: Feb. 7, 2023

(54) MELTING DEVICE AND MELTING METHOD

(71) Applicant: TERUMO KABUSHIKI KAISHA, Tokyo (JP)

(72) Inventor: Yusuke Nozaki, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 241 days.

(21) Appl. No.: 17/014,610

(22) Filed: Sep. 8, 2020

(65) Prior Publication Data

US 2020/0398281 A1 Dec. 24, 2020

Related U.S. Application Data

(63) Continuation of application No. PCT/JP2019/009307, filed on Mar. 8, 2019.

(30) Foreign Application Priority Data

Mar. 13, 2018 (JP) .............................. JP2018-045044

(51) Int. Cl.
    *B01L 7/04* (2010.01)

(52) U.S. Cl.
    CPC ......... *B01L 7/04* (2013.01); *B01L 2200/0689* (2013.01); *B01L 2300/123* (2013.01); *B01L 2300/14* (2013.01); *B01L 2300/185* (2013.01); *B01L 2400/049* (2013.01)

(58) Field of Classification Search
    CPC .......... A61M 1/0281; A61M 2205/366; A61M 5/445; B01L 2200/0689; B01L 2300/123; B01L 2300/14; B01L 2300/185; B01L 2400/049; B01L 7/00; B01L 7/04; A01N 1/0242
    See application file for complete search history.

(56) References Cited

U.S. PATENT DOCUMENTS

2004/0053186 A1 3/2004 Miyagawa
2007/0127901 A1 6/2007 Kuzyk
(Continued)

FOREIGN PATENT DOCUMENTS

| EP | 0318924 A | 6/1989 |
|---|---|---|
| JP | 47-006712 Y | 3/1972 |
| JP | 2001-070402 A | 3/2001 |

(Continued)

OTHER PUBLICATIONS

Fujisawa Toshimasa, JP 2007061245A Device for thawing Frozen Plasma translation, Mar. 2007, Espacenet, Description (Year: 2007).*

(Continued)

*Primary Examiner* — Jennifer Wecker
*Assistant Examiner* — Mickey Huang
(74) *Attorney, Agent, or Firm* — Jason H. Vick; Sheridan Ross, PC

(57) ABSTRACT

A melting device is provided that melts a bio-derived frozen product contained in a container including a heat transfer section comprising at least two heating bags, each of which is filled with a heating liquid and is capable of sandwiching the container between the at least two heating bags and a suction mechanism that sucks air from a space between the at least two heating bags and surrounding the container.

19 Claims, 2 Drawing Sheets

(56) References Cited

U.S. PATENT DOCUMENTS

2013/0177683 A1     7/2013   Shei et al.
2015/0122793 A1     5/2015   Takizawa

FOREIGN PATENT DOCUMENTS

| JP | 2001070402 A | * | 3/2001 | ............ C12M 47/20 |
| JP | 2004-103480 A | | 4/2004 | |
| JP | 2007-061245 A | | 3/2007 | |
| JP | 2007061245 A | * | 3/2007 | |
| JP | 2014-151140 A | | 8/2014 | |

OTHER PUBLICATIONS

Saito Kenichi, JP 2001070402 A Bag and Method for thawing Frozen Cell translation, Mar. 2001, Espacenet, Description (Year: 2001).*

International Preliminary Report on Patentability for International Application No. PCT/JP2019/009307, dated Sep. 15, 2020.

International Search Report for International Application No. PCT/JP2019/009307, dated May 28, 2019.

Written Opinion for International Application No. PCT/JP2019/009307, dated May 28, 2019.

* cited by examiner

MELTING DEVICE AND MELTING METHOD

CROSS REFERENCE TO RELATED APPLICATIONS

The present application is a continuation of and claims benefit to PCT Application No. PCT/JP2019/009307 filed on Mar. 8, 2019, entitled "MELTING DEVICE AND MELTING METHOD" which claims priority to Japanese Patent Application No. 2018-045044 filed on Mar. 13, 2018. The entire disclosures of the applications listed above are hereby incorporated herein by reference, in their entirety, for all that they teach and for all purposes.

FIELD

The present disclosure relates to a melting device and a melting method for melting a bio-derived frozen product contained in a container.

BACKGROUND

Conventionally, a method of immersing a container in a constant temperature water tank is generally used to melt (e.g., thaw, unfreeze, etc.) a bio-derived frozen product such as a frozen cell contained in the container such as a bag. However, there is a concern regarding a hygienic problem in such a melting method using hot water. European Patent Application No. 0318924 proposes a device that sandwiches a container from above and below with two heating bags and melts a bio-derived frozen product in the container.

SUMMARY

In the related art, however, the heat transfer from the heating bag to the container is not efficiently performed, so it takes a long time to melt the bio-derived frozen product.

The present disclosure has been made in consideration of such problems, and an object thereof is to provide a melting device and a melting method capable of hygienically and quickly melting a bio-derived frozen product contained in a container.

In order to achieve the above object, one aspect of the present disclosure is a melting device that melts a bio-derived frozen product contained in a container and includes: a heat transfer section that has at least two heating bags, wherein each of the at least two heating bags comprises a storage chamber containing, or configured to contain, a heating liquid and is capable of sandwiching the container between the at least two heating bags; and a suction mechanism (e.g., a vacuum, etc.) that sucks air (e.g., from a space) between the at least two heating bags and surrounding the container and removes the air out of the heat transfer section.

According to this melting device, the air between the two heating bags is sucked by the suction mechanism, and thus, adhesion between the container and the two heating bags constituting the heat transfer section can be enhanced, and heat transfer from the heat transfer section to the container can be promoted. Therefore, it is possible to rapidly melt the bio-derived frozen product contained in the container. In addition, it is hygienic since the heating liquid does not come into direct contact with an outer surface of the container.

The above melting device may include a holding mechanism that sandwiches outer circumferential portions of the at least two heating bags in a thickness direction to be overlapped, and wherein the outer circumferential portions come into close contact with each other when sandwiched.

With this arrangement, the adhesion between the container and the heat transfer section can be further enhanced, and the air between the two heating bags can be more efficiently sucked, or removed, from a space between the two heating bags and the container.

In the above melting device, at least one of the outer circumferential portions of the at least two heating bags may be provided with a seal member made of an elastic (e.g., elastomeric) body over the whole circumference.

With this arrangement, airtightness of the outer circumferential portions of the two heating bags can be enhanced, and the air between the two heating bags can be more efficiently sucked, or removed, from a space between the two heating bags and the container.

The above melting device may include: a main body to which one of the at least two heating bags is attached; and a lid to which the other of the at least two heating bags is attached and which is capable of being open and closed with respect to the main body. The holding mechanism may include a first holding portion provided on the main body and a second holding portion provided on the lid, and the outer circumferential portions of the at least two heating bags may be sandwiched by the first holding portion and the second holding portion as the lid is closed with respect to the main body.

With this arrangement, the outer circumferential portions of the at least two heating bags can be brought into close contact with each other by a simple operation.

In the above melting device, the suction mechanism may include an air intake tube arranged between the at least two heating bags.

As a result, the air between the two heating bags can be efficiently sucked (or removed, from a space between the two heating bags and the container) with a simple configuration.

Another aspect of the present disclosure is a melting method for melting a bio-derived frozen product contained in a container, and the melting method includes: sandwiching the container between a first heating bag and a second heating bag, wherein each of the first heating bag and the second heating bag is filled with a heating liquid; and applying a vacuum to an area between the first heating bag and the second heating bag removing air from a space between the first heating bag and the second heating bag and surrounding the container sandwiched between the first heating bag and the second heating bag. For instance, the air in a space between the two heating bags and surrounding the container may be removed, via a vacuum, causing surfaces of the two heating bags to directly contact surfaces of the container. This direct contact between the surfaces of the two heating bags and container provides an enhanced heat conduction surface area when compared to a system that does not remove the air from the space.

According to the melting device and the melting method of the present disclosure, it is possible to hygienically and rapidly melt the bio-derived frozen product contained in the container.

In yet another aspect of the present disclosure a system is provided for melting a bio-derived frozen product contained in a container, the system comprising: a control unit; and a melting device, the melting device comprising: a heat transfer section comprising a first heating bag and a second heating bag, each of the first heating bag and the second heating bag comprising a storage chamber containing a heating liquid; and a suction mechanism comprising an air intake tube, the air intake tube disposed in an area between the first heating bag and the second heating bag.

DETAILED DESCRIPTION

Hereinafter, embodiments of a melting device and a melting method according to the present disclosure will be described with reference to the accompanying drawings.

Figure 1:
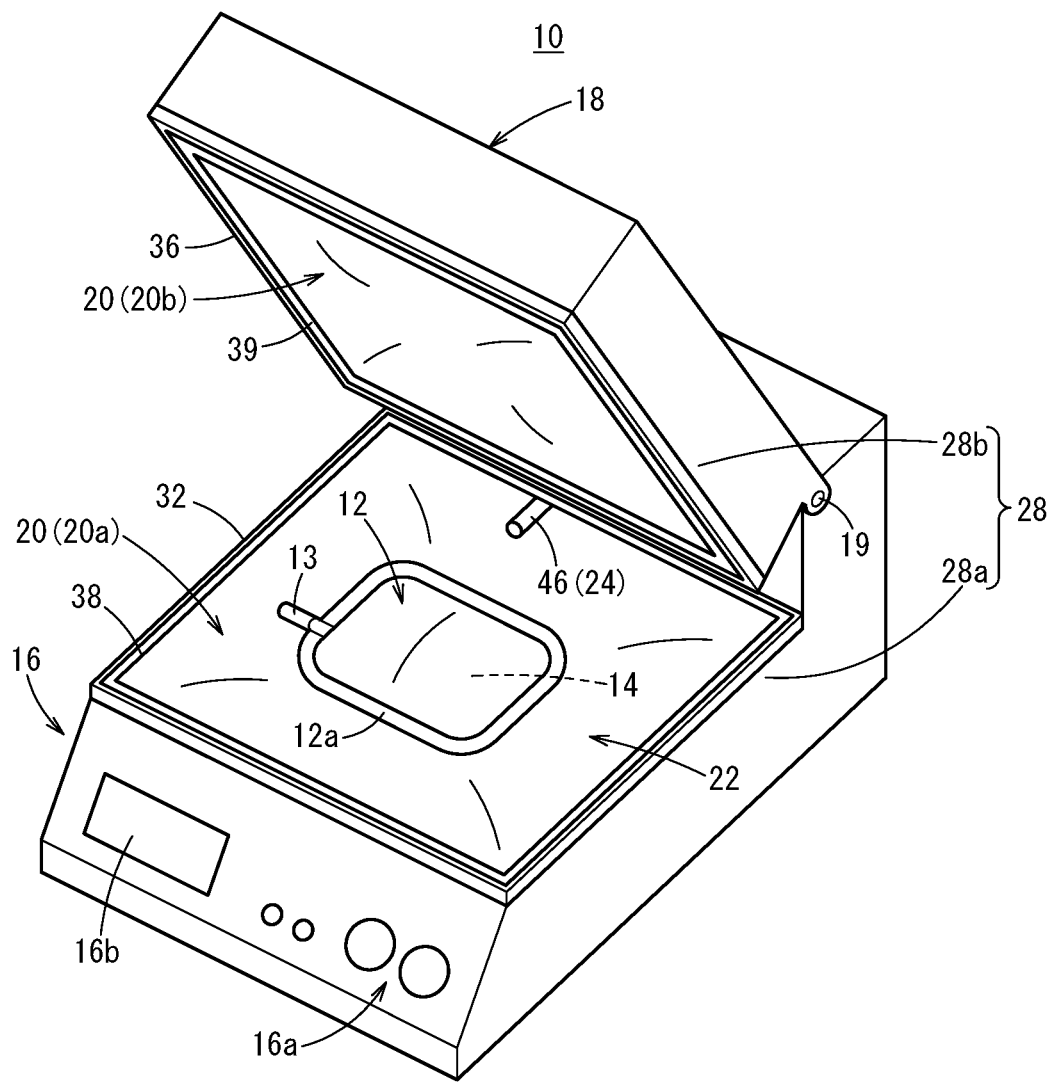
FIG. 1 is a perspective view of a melting device according to an embodiment of the present disclosure.
Figure 2:
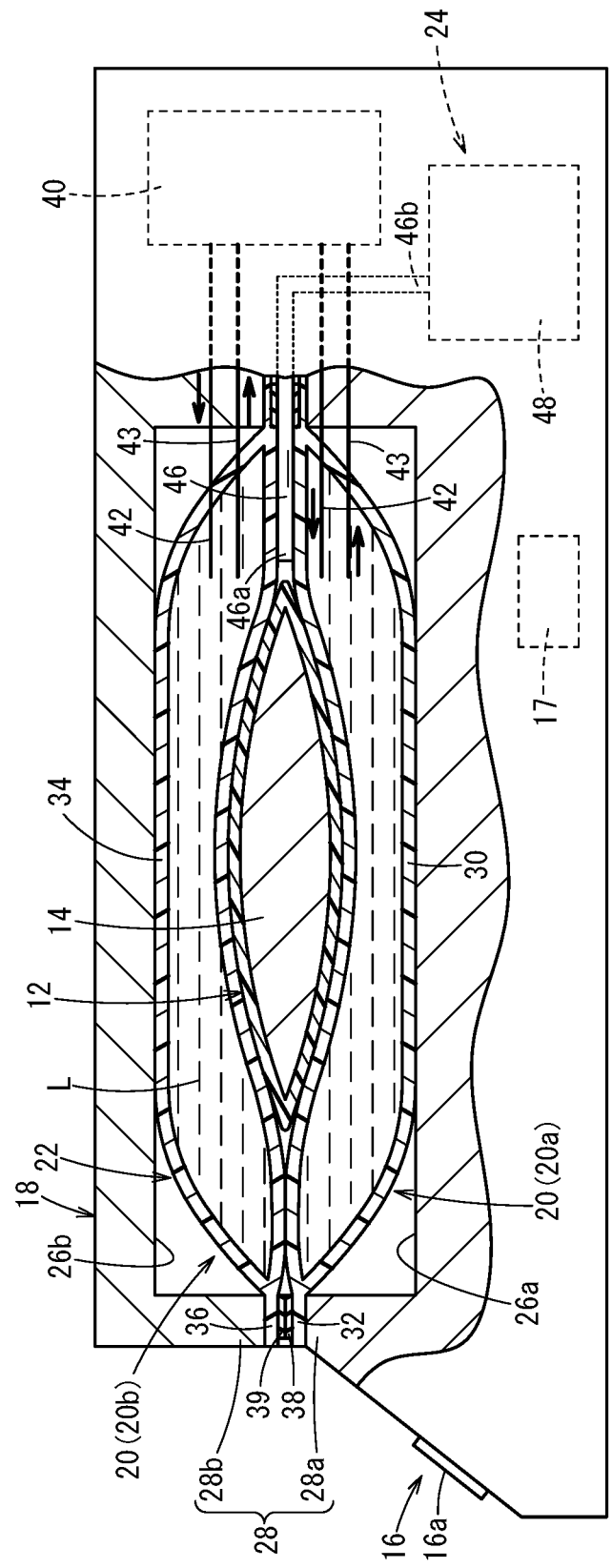
FIG. 2 is a schematic cross-sectional view (partial cross-sectional view) of the melting device.

A melting device 10 according to an embodiment illustrated in FIGS. 1 and 2 is used to melt a bio-derived frozen product 14 contained in a container 12. The container 12 is, for example, a bag-shaped flat soft bag formed of a resin film. The bio-derived frozen product 14 contained in the container 12 is obtained by freezing a liquid containing a bio-derived substance (bio-derived liquid product).

Examples of the bio-derived liquid product include a cell suspension, blood, plasma, and the like. Examples of the cell suspension may include hematopoietic stem cells (e.g., umbilical cord blood, bone marrow fluid, a peripheral blood stem cell, and the like) which may be used for stem cell transplantation. Cells in the cell suspension are not limited thereto, and are cells such as adherents cells such as myoblasts, cardiomyocytes, fibroblasts, synovial cells, epithelial cells, endothelial cells, hepatocytes, pancreatic cells, renal cells, adrenal cells, periodontal ligament cells, gingival cells, periosteal cells, skin cells, and chondrocytes, blood cells and blood components such as whole blood, red blood cells, white blood cells, lymphocytes (T lymphocytes, B lymphocytes), dendritic cells, plasma, platelets, and platelet-rich plasma, bone marrow derived mononuclear cells, hematopoietic stem cells, ES cells, pluripotent stem cells, iPS cell-derived cells (for example, iPS cell-derived cardiomyocytes), mesenchymal stem cells (for example, those derived from bone marrow, adipose tissue, peripheral blood, skin, hair root, muscle tissue, endometrium, placenta, cord blood, and the like), and/or gametes (e.g., sperm cells and/or egg cells). These cells may be cells into which a gene used for gene therapy or the like has been introduced. A port 13 configured to extract a bio-derived liquid product from the inside of the container 12 is provided in a circumferential edge portion 12a of the container 12.

The melting device 10 includes: a main body 16; a lid 18 movably connected to the main body 16; a heat transfer section 22 having at least two heating bags 20; and a suction mechanism 24 (e.g., a vacuum, etc.) that sucks, or removes, air from a space between the two heating bags 20.

As illustrated in FIG. 1, the main body 16 is provided with: an operation section 16a including an operation button configured to operate operation start, operation stop, and the like, and setting buttons for various settings; and a display 16b that displays various types of information (e.g., set time, remaining time, set temperature, and the like). The lid 18 may be rotatably connected to the main body 16 via a hinge portion 19 and can be open and closed with respect to the main body 16. Additionally or alternatively, a lock mechanism (e.g., a hook, latch, etc.) configured to maintain the melting device 10 in a closed state when the lid 18 is closed may be provided.

As illustrated in FIG. 2, the main body 16 has a first concave portion 26a, or cavity, in which one of the two heating bags 20 (hereinafter, also referred to as a "first bag 20a") is arranged, and a frame-shaped first holding portion 28a that protrudes upward with respect to the first concave portion 26a. The lid 18 has a second concave portion 26b in which the other bag of the two heating bags 20 (hereinafter, also referred to as a "second bag 20b") is arranged, and a frame-shaped second holding portion 28b that protrudes downward with respect to the second concave portion 26b.

The first bag 20a and the second bag 20b are filled with a heating liquid L (e.g., water, etc.). The first bag 20a and the second bag 20b are soft bags that are made of, for example, a resin film and are easily deformed. Each of the first bag 20a and the second bag 20b is substantially flat, or has a flat shape as a whole and is substantially rectangular or may be formed in a quadrangular shape in a plan view. The first bag 20a and the second bag 20b may be formed in a shape other than the quadrangular or substantially rectangular shape in a plan view, for example, the first bag 20a and the second bag 20b may have a circular shape, an elliptical shape, or the like.

The first bag 20a has a bag-shaped liquid chamber forming portion 30 that forms a liquid chamber (e.g., storage chamber) therein, and a plate-shaped outer circumferential portion 32 that surrounds the outer circumference of the liquid chamber forming portion 30. Similarly, the second bag 20b also has a bag-shaped liquid chamber forming portion 34 that forms a liquid chamber, and a plate-shaped outer circumferential portion 36 that surrounds the outer circumference of the liquid chamber forming portion 34. In some embodiments, the first bag 20a and the second bag 20b may have the same size and the same shape in a plan view. When the first bag 20a is at least partially filled with the heating liquid, L, the bag-shaped liquid chamber forming portion 30 may bulge outwardly from a center of the first bag 20a in an area inside the plate-shaped outer circumferential portion 32. When the second bag 20b is at least partially filled with the heating liquid, L, the bag-shaped liquid chamber forming portion 34 may bulge outwardly from a center of the second bag 20b in an area inside the plate-shaped outer circumferential portion 36.

The first bag 20a is supported by the main body 16. Therefore, the first bag 20a can also be referred to herein as a lower bag. The liquid chamber forming portion 30 of the first bag 20a is arranged in the first concave portion 26a of the main body 16. The first holding portion 28a of the main body 16 is formed in a shape corresponding to the outer circumferential portion 32 of the first bag 20a, and the outer circumferential portion 32 of the first bag 20a is supported by the first holding portion 28a of the main body 16. A first seal member 38 made of an elastic body (e.g., a rubber, silicone, urethane, or other elastomeric material, etc.) is arranged on the outer circumferential portion 32 of the first bag 20a. The first seal member 38 is provided on the outer circumferential portion 32 of the first bag 20a over the whole circumference. The first seal member 38 is formed in a plate shape.

The second bag 20b is supported by the lid 18. Therefore, the second bag 20b can be referred to herein as an upper bag. The liquid chamber forming portion 34 of the second bag 20b is arranged in the second concave portion 26b of the lid 18. The second holding portion 28b of the lid 18 is formed in a shape corresponding to the outer circumferential portion 36 of the second bag 20b, and the outer circumferential portion 36 of the second bag 20b is supported by the second holding portion 28b of the lid 18. A second seal member 39 made of an elastic body (e.g., a rubber, silicone, urethane, or other elastomeric material, etc.) may be arranged on the outer circumferential portion 36 of the second bag 20b. The second seal member 39 is provided on the outer circumferential portion 36 of the second bag 20b over the whole circumference. The second seal member 39 is formed in a plate shape.

Additionally or alternatively, the first bag 20a may be made up of a plurality of sub-bags arranged in parallel with the main body 16. Additionally or alternatively, the second bag 20b may be made up of a plurality of sub-bags arranged in parallel with the lid 18. Therefore, in some embodiments the heat transfer section 22 may comprise three or more heating bags 20.

When the lid 18 is closed (e.g., positioned in the closed state) as illustrated in FIG. 2, the outer circumferential portion 32 of the first bag 20a and the outer circumferential portion 36 of the second bag 20b overlap each other, and the outer circumferential portions 32 and 36 are sandwiched from above and below by the first holding portion 28a and the second holding portion 28b, so that the first seal member 38 and the second seal member 39 abut on each other. The first holding portion 28a and the second holding portion 28b form a holding mechanism 28 that sandwiches the outer circumferential portion 32 of the first bag 20a and the outer circumferential portion 36 of the second bag 20b.

The main body 16 is provided with a heating circulation unit 40 (e.g., a fluid heater, thermal fluid heater, heat pump, etc.) that heats the liquid L to a predetermined temperature or temperature range (e.g., 30° C. to 40° C.) and supplies the heated liquid L to the first bag 20a and the second bag 20b, and moves, conveys, or circulates, the liquid L from the first bag 20a and the second bag 20b (e.g., to the heating circulation unit 40, etc.) to reheat the liquid L (e.g., once the liquid L has discharged heat). The liquid L heated to the predetermined temperature in the heating circulation unit 40 may be sent to the first bag 20a and the second bag 20b via introduction tubes 42 connected to the first bag 20a and the second bag 20b, respectively. The liquid L is returned from the first bag 20a and the second bag 20b to the heating circulation unit 40 via an extraction tube 43. The heating circulation unit 40 is controlled by a control unit 17 provided in the main body 16. In some embodiments, the heating circulation unit 40 may be an external device provided separately from the main body 16 instead of being a part of the main body 16.

FIG. 2 schematically illustrates the connection between each of the first bag 20a and the second bag 20b and each of the introduction tube 42 and the extraction tube 43. In some embodiments, the introduction tube 42 and the extraction tube 43 are connected to the outer circumferential portions 32 and 36, respectively, so as to penetrate the outer circumferential portions 32 and 36 of the first bag 20a and the second bag 20b.

The suction mechanism 24, or vacuum, has an air intake tube 46 and an air intake pump 48. The air intake tube 46 has a first end 46a that is one end and a second end 46b that is the other end. The air intake tube 46 is arranged such that the first end 46a is located between the first bag 20a and the second bag 20b in a state (e.g., overlapping state) where the first bag 20a and the second bag 20b are closed. The second end 46b of the air intake tube 46 is connected to the air intake pump 48. The air intake pump 48 is controlled by the control unit 17. In some embodiments, the suction mechanism 24 may be an external device provided separately from the main body 16 instead of being a part of the main body 16.

Next, an operation of the melting device 10 configured as described above (e.g., a melting method according to embodiments of the present disclosure) will be described.

When a bio-derived frozen product 14 contained in the container 12 is melted using the melting device 10, the lid 18, in an open state, may provide access to the space between the first bag 20a and the second bag 20b. While the lid 18 is open, the container 12 in which the bio-derived frozen product 14 is stored may be placed on the first bag 20a as illustrated in FIG. 1. Then, the lid 18 is closed and the container 12 is sandwiched between the first bag 20a and the second bag 20b as illustrated in FIG. 2. As the lid 18 is closed, the outer circumferential portions 32 and 36 of the first bag 20a and the second bag 20b are sandwiched from above and below by the first holding portion 28a and the second holding portion 28b. As a result, the first seal member 38 and the second seal member 39 arranged on the outer circumferential portions 36 of the first bag 20a and the second bag 20b abut on each other and are brought into close contact with each other. In this case, the air intake tube 46 is sandwiched between the outer circumferential portions 32 and 36 of the first bag 20a and the second bag 20b (e.g., between the first seal member 38 and the second seal member 39).

When a start button of the operation section 16a provided in the main body 16 is operated (e.g., pushed), the melting device 10 starts operating. Specifically, the heated liquid L (e.g., heated by the heating circulation unit 40) is introduced into the first bag 20a and the second bag 20b so that the first bag 20a and the second bag 20b are heated. The bio-derived frozen product 14 in the container 12 sandwiched between the first bag 20a and the second bag 20b is heated from above and below by the first bag 20a and the second bag 20b. As described above, the heat transfer section 22 heats the bio-derived frozen product 14 in the container 12, and the heating is maintained for a certain period of time to melt the bio-derived frozen product 14.

In parallel with the heating by the heat transfer section 22, the suction mechanism 24, or vacuum, also operates. Specifically, the air intake pump 48 operates so that air in a space between the first bag 20a and the second bag 20b and surrounding the container 12 is sucked out, or removed, by the air intake tube 46. As a result, a wall portion forming the liquid chamber forming portion 30 of the first bag 20a is brought into close contact with an outer surface of the container 12, and a wall portion forming the liquid chamber forming portion 34 of the second bag 20b is brought into close contact with the outer surface of the container 12.

According to the melting device 10, since the air between the two heating bags 20 is sucked out, or removed, by the suction mechanism 24, the adhesion (e.g., surface area contact) between the container 12 and each of the two heating bags 20 forming the heat transfer section 22 can be enhanced, and the heat transfer from the heat transfer section 22 to the container 12 can be promoted. That is, the bio-derived frozen product 14 in the container 12 can be efficiently heated by removing an air layer between the container 12 and the heat transfer section 22. Therefore, it is possible to rapidly melt the bio-derived frozen product 14 contained in the container 12. In addition, the melting device 10 provides for hygienic operation since the heating liquid L does not come into direct contact with the outer surface of the container 12. In some embodiments, removing the air from the space between the first bag 20a and the second bag 20b and surrounding the container 12 may force contacting surfaces of the first bag 20a and the second bag 20b with the container 12 to completely surround and contact all of the exterior surfaces of the container 12.

The melting device 10 includes the holding mechanism 28 that sandwiches the outer circumferential portions 32 and 36 of the two heating bags 20 in a thickness direction to be overlapped so as to bring the outer circumferential portions 32 and 36 into close contact with each other. With this configuration, the adhesion (e.g., surface area contact, etc.) between the container 12 and the heat transfer section 22 can be further enhanced, and the air between the two heating bags 20 can be more effectively removed.

The first and second seal members 38, 39, each of which is made of the elastic body, are provided on the outer circumferential portions 32 and 36 of the two heating bags 20, respectively, over the whole circumference. With this configuration, the airtightness of the outer circumferential portions 32 and 36 of the two heating bags 20 can be enhanced, and the air between the two heating bags 20 can be more effectively sucked. Additionally or alternatively, only one of the first and second seal members 38 and 39 may be provided.

The holding mechanism 28 has the first holding portion 28a provided on the main body 16 and the second holding portion 28b provided on the lid 18, and the outer circumferential portions 32 and 36 of the two heating bags 20 are sandwiched by the first holding portion 28a and the second holding portion 28b as the lid 18 is closed. With this configuration, the outer circumferential portions 32 and 36 of the two heating bags 20 can be brought into close contact with each other by a simple operation.

The present disclosure is not limited to the above-described embodiment, and various modifications can be made within a scope not departing from a gist of the present disclosure.

What is claimed is:

1. A melting device that melts a bio-derived frozen product contained in a container, the melting device comprising:
    a heat transfer section comprising at least two heating bags, wherein each of the at least two heating bags comprises a storage chamber containing a heating liquid, and wherein the heat transfer section sandwiches the container between the at least two heating bags; and
    a suction mechanism configured to suck air from a space between the at least two heating bags and surrounding the container and further configured to remove the air out of the heat transfer section.

2. The melting device of claim 1, further comprising:
    a holding mechanism that sandwiches outer circumferential portions of the at least two heating bags in a thickness direction to be overlapped, and wherein the outer circumferential portions come into close contact with each other when sandwiched.

3. The melting device of claim 2, wherein
    at least one of the outer circumferential portions of the at least two heating bags is provided with a seal member made of an elastic body over a whole circumference.

4. The melting device of claim 2, further comprising:
    a main body to which one of the at least two heating bags is attached; and
    a lid to which the other of the at least two heating bags is attached, and which is capable of being open and closed with respect to the main body, wherein
    the holding mechanism includes a first holding portion provided on the main body and a second holding portion provided on the lid, and
    the outer circumferential portions of the at least two heating bags are sandwiched by the first holding portion and the second holding portion as the lid is closed with respect to the main body.

5. The melting device of claim 1, wherein the suction mechanism has an air intake tube arranged between the at least two heating bags.

6. The melting device of claim 5, wherein the suction mechanism is controlled by a control unit.

7. The melting device of claim 5, wherein the at least two heating bags comprises a first heating bag and a second heating bag, and wherein the melting device further comprises:
    a heating circulation unit, the heating circulation unit comprising a first introduction tube, a second introduction tube, and a first extraction tube, and a second extraction tube, wherein the first introduction tube and the first extraction tube are in fluidic communication with the first heating bag, and wherein the second introduction tube and the second extraction tube are in fluidic communication with the second heating bag.

8. The melting device of claim 7, wherein the heating circulation unit circulates the heating liquid in a heated state into the first heating bag via the first introduction tube and into the second heating bag via the second introduction tube, and wherein the heating circulation unit circulates the heating liquid in an unheated state out of the first heating bag via the first extraction tube and out of the second heating bag via the second extraction tube.

9. A melting method for melting a bio-derived frozen product contained in a container, the melting method comprising:
    sandwiching the container between a first heating bag and a second heating bag, wherein each of the first heating bag and the second heating bag is filled with a heating liquid; and
    applying a vacuum to an area between the first heating bag and the second heating bag removing air from a space between the first heating bag and the second heating bag and surrounding the container sandwiched between the first heating bag and the second heating bag.

10. The melting method of claim 9, wherein a holding mechanism sandwiches a first outer circumferential portion of the first heating bag with a second outer circumferential portion of the second heating bag in a first direction, and wherein the first outer circumferential portion and the second outer circumferential portion come into close contact with each other when sandwiched together.

11. The melting method of claim 10, wherein the at least one of the first outer circumferential portion and the second outer circumferential portion comprises a seal, wherein the seal is disposed circumferentially about the at least one of the first outer circumferential portion and the second outer circumferential portion.

12. The melting method of claim 10, wherein the first heating bag is disposed within a main body of a melting device, wherein the second heating bag is attached to a lid of the melting device, wherein the lid is pivotally attached to the main body, wherein the holding mechanism comprises a first holding portion disposed on the main body and a second holding portion disposed on the lid, and wherein the first holding portion sandwiches the first outer circumferential portion and the second portion sandwiches the second outer circumferential portion when the lid is pivoted toward the main body in a closed state.

13. The melting method of claim 9, wherein the vacuum is applied by a suction mechanism comprising an air intake tube positioned between the first heating bag and the second heating bag.

14. A system for melting a bio-derived frozen product contained in a container, the system comprising:
a control unit; and
a melting device, the melting device comprising:
a heat transfer section comprising a first heating bag and a second heating bag, each of the first heating bag and the second heating bag comprising a storage chamber containing a heating liquid; a holding mechanism operable to sandwich a first outer circumferential portion of the first heating bag and a second outer circumferential portion of the second heating bag together in a first direction; and
a suction mechanism comprising an air intake tube, the air intake tube disposed in an area between the first heating bag and the second heating bag, and wherein the suction mechanism is configured to suck air from a space between the at least two heating bags and surrounding the container and further configured to remove the air out of the heat transfer section.

15. The system of claim 14, wherein at least one of the first outer circumferential portion and the second outer circumferential portion comprises an elastomeric seal.

16. The system of claim 15, wherein the elastomeric seal is disposed circumferentially about the at least one of the first outer circumferential portion and the second outer circumferential portion.

17. The system of claim 15, wherein the melting device further comprises:
a main body; and
a lid hinged to the main body, the lid movable between an open state and a closed state,
wherein the holding mechanism comprises a first holding portion disposed on the main body and attached to the first heating bag, and a second holding portion disposed on the lid and attached to the second heating bag, and
wherein, when the lid is pivoted toward the main body and positioned in the closed state, the first holding portion and the second holding portion sandwich the first outer circumferential portion and the second outer circumferential portion together in the first direction.

18. The system of claim 17, wherein the melting device further comprises:
a heating circulation unit, the heating circulation unit comprising a first introduction tube, a second introduction tube, and a first extraction tube, and a second extraction tube,
wherein the first introduction tube and the first extraction tube are in fluidic communication with the first heating bag, and wherein the second introduction tube and the second extraction tube are in fluidic communication with the second heating bag.

19. The system of claim 18, wherein the control unit operates the heating circulation unit to circulate the heating liquid in a heated state into the first heating bag via the first introduction tube and into the second heating bag via the second introduction tube, and wherein the control unit operates the heating circulation unit to circulate the heating liquid out of the first heating bag via the first extraction tube and out of the second heating bag via the second extraction tube.

* * * * *